United States Patent [19]

Hack et al.

[11] Patent Number: 5,133,772
[45] Date of Patent: Jul. 28, 1992

[54] FEMORAL IMPLANT FOR HIP ARTHROPLASTY

[75] Inventors: Bradford H. Hack, Arcadia; Philip O. Merritt, Los Angeles, both of Calif.

[73] Assignee: Osteonics Corporation, Allendale, N.J.

[21] Appl. No.: 466,036

[22] Filed: Jan. 17, 1990

[51] Int. Cl.⁵ ............................................ A61F 2/32
[52] U.S. Cl. .................................................... 623/23
[58] Field of Search ................ 623/16, 18, 20, 21, 623/22; 606/92, 93, 94, 95

[56] References Cited

U.S. PATENT DOCUMENTS

| | | | |
|---|---|---|---|
| 4,494,535 | 1/1985 | Haig | 606/94 |
| 4,653,487 | 3/1987 | Maale | 606/62 |
| 4,753,657 | 6/1988 | Lee et al. | 623/23 |
| 4,988,359 | 1/1991 | Frey et al. | 623/23 |

FOREIGN PATENT DOCUMENTS

2654524 11/1988 France .......................... 623/23
1424829 9/1988 U.S.S.R. ........................ 623/16

Primary Examiner—David J. Isabella

[57] ABSTRACT

The present invention concerns a femoral hip prosthetic implant, and a process, that incorporates an interior channel in the implant, which channel permits the implant, after it is properly positioned in a canal at the proximal end of a prepared femur, to be left in that position. Cement is then injected through that channel and discharged through medial ports in the implant to flood and up-well in the space between the implant and the femoral canal, thereby bonding and sealing the implant to the proximal portion of the femur while the implant remains seated in the desired position within the femur. Preferably a collar is provided at the distal portion of the stem to firmly seat and center the stem within the femoral canal. Also, preferably a spacer is provided at the mid-portion of the stem to center the stem within the femoral canal and to prevent cement from passing down the femoral canal beyond the proximal end of the stem.

12 Claims, 2 Drawing Sheets

FEMORAL IMPLANT FOR HIP ARTHROPLASTY

BACKGROUND

The present invention relates to an improved femoral hip prosthetic implant and to a process for securing a hip prosthetic implant to the proximal end of the femur.

Total hip arthroplasty, or hip replacement, during the last few decades has evolved into a standard orthopedic procedure; it is estimated that approximately 100,000 hip replacements are performed yearly in the United States and almost four times that amount world wide. Success rates are consistently reported to be greater than 90% and are accompanied by dramatic reduction in the patient's pain and disability.

While total hip replacement works well and relieves pain, it is not entirely without problems. One common problem is that the femoral implant loosens from the femoral canal. Also, in approximately 3% of the implants, post operative dislocation of the head of the femur from the acetabular cup may occur. Both of these problems, loosening of the femur, and dislocation of the hip joint—are believed to arise from an underlying problem presented by all the various techniques for performing hip arthroplasty. These techniques require the surgeon to prepare a socket in the proximal end of the femur for receiving the distal end of the implant, then to fill that socket either partially or totally with a cement, then to force the stem end portion of the implant into the prepared socket while the cement is still in a workable condition and to accurately position the implant so that its head will seat properly in the acetabular cup, all before the cement hardens.

The present invention has as a major objective the provision of a femoral implant, and a process for securing a femoral implant in the proximal end of the femur, such that the implant is accurately and stably positioned within the femur, using a simple and reproducible procedure, to achieve a uniform thickness of the cement mantle surrounding the implant and to completely fill the proximal space between the implant and the femur. Another object of the present invention is to provide an implant and procedure which, should it become necessary to replace the implant, permits the implant to be easily removed and all of the cement cleaned from the femoral canal with minimum loss of bone tissue.

These and other objects will be apparent to those skilled in this art from the following detailed description of a preferred embodiment of the invention.

BRIEF SUMMARY OF THE INVENTION

The present invention provides a femoral hip prosthetic implant having a body terminating at the proximal end in a Morse taper neck portion for receiving a head, and at the distal end in a stem portion. The implant includes at least one interior channel terminating in at least one port communicating with the exterior surface of the implant at its mid-portion and adjacent to the cavity in the femur for receiving the implant, and means for receiving and directing cement under pressure into the interior channel from the proximal end of the implant after the implant has been properly positioned in the femoral canal. As a result of this construction of the implant, the implant first may be accurately position in the prepared femoral canal then, while the implant is still properly positioned, cement is forced through the interior channel to flood the proximal end of the cavity prepared in the femoral canal and to well up under pressure in that cavity to secure the implant to the femur. Preferably sealing mans are also provided between the mid-portion of the implant and the femoral canal to prevent cement from flowing distally down the canal beyond the seal.

The present invention also provides a process for securing a femoral hip prosthetic implant within on a medullary cavity prepared in a femur employing an implant having an interior channel; the process includes the steps of first positioning the implant in the prepared femoral canal to properly locate it relative to the femur and to provide adequate space surrounding the implant, then forcing cement under pressure through the channel in the implant to flood the proximal space between the implant and the interior of the femur and to well up about the implant to provide a collar of cement surrounding the implant at the proximal end of the femur and to secure the implant to the femur.

BRIEF DESCRIPTION OF THE DRAWINGS

The invention will be further described in connection with the accompanying drawings, in which.

DETAILED DESCRIPTION

The femoral implant of the present invention permits the orthopedic surgeon to employ a new, simple and effective technique for properly positioning and securing the implant within the femur. As will be explained in more detail, the implant incorporates an interior channel for receiving cement under pressure, and for discharging that cement through ports into the mid-portion of the cavity prepared in the femur to receive the cement. As a result, the implant can be carefully and accurately positioned in the femur by the surgeon, and the positioning checked to make sure that the implant is properly located. The surgeon is under no time pressure while this is being done, such as would be imposed if the cement were already in the femoral canal and in the process of solidifying. When the surgeon is satisfied that the implant is properly positioned in the femur, it is left in that position. The cement is then prepared and injected through the interior cavity in the implant to pass through ports in the implant and to flood the proximal portion of the cavity between the implant and the femur, preferably from the mid-portion of the implant up to its proximal end. This upwelling of cement in the femur tends to carry up and out of the femoral cavity any blood, tissue or bone chips which may remain in it and which would otherwise significantly weaken the bolus of cement flooding the interior cavity, and the resultant cement bone interface.

Since the cement may be injected into the cavity shortly after mixing, and without requiring it to have set sufficiently to lose its initial stickiness, the cement is more liquid and free flowing using the present technique than would otherwise be the case, which in turn achieves improved penetration of the cement into the cancellous structure of the femur, and an improved bonding of the implant to the femur. Further, the present femoral implant and technique insures that a collar of cement of relatively uniform thickness will be provided about the proximal end of the implant and between the implant and femoral cavity, which in turn is believed to significantly improve the durability and life of the implant, and thereby improve the success of the procedure.

Figures 1, 3:
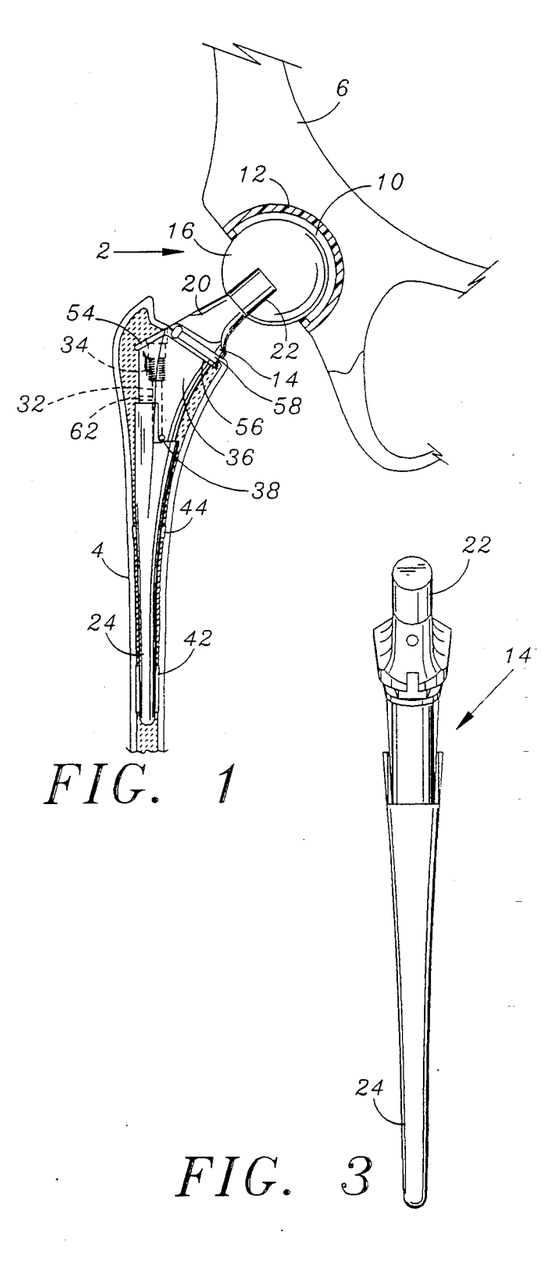
FIG. 1 is a plan view of the femoral implant of the present invention, showing its relation to the femur, the acetabular cup and the adjacent pelvic structure.
FIG. 3 is a front view of the femoral implant.
Figure 2:
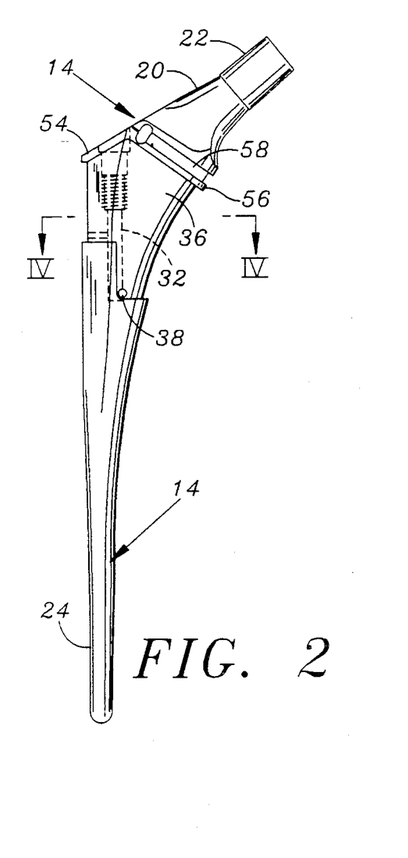
FIG. 2 is a side view of the femoral implant of the present invention.
Figure 4:
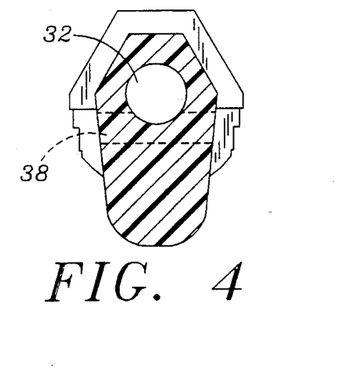
FIG. 4 is cross-sectional view taken on line IV-IV of FIG. 2.
Figure 5:
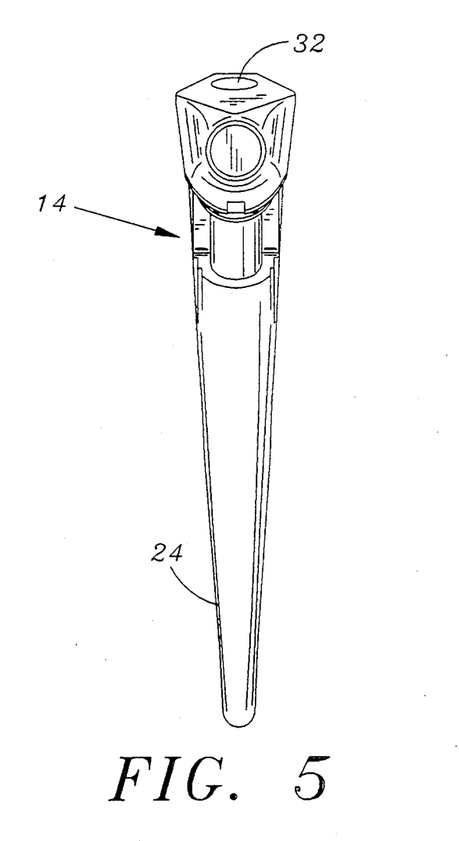
FIG. 5 is a perspective view of the femoral implant.

The implant, and its relationship to the bone structure which forms the human hip joint, is generally illustrated in FIG. 1. As there shown, the hip joint 2 receives the head of the femur 4 in the acetabular socket of the pelvic structure 6. The hip replacement operation commonly replaces both the acetabular socket and the proximal end portion of the femur, including the head of the femur. When replaced, the acetabular cup commonly includes a hemispherical socket 10 secured to the adjacent pelvic bone structure by cement 12, and an implant 14 received in a socket prepared in the proximal end of the femur, the implant in turn receiving a sphere 16 that seats in the hemispherical socket 10 to form the new hip joint.

The structure of the preferred implant of the present invention is illustrated in FIGS. 2 to 5. As they show, the implant 14 consists of neck portion 20 that terminates in a Morse taper 22 which receives and supports head 16. At its distal end, the implant terminates in a stem portion 24 received in the femoral or medullary canal.

During the hip replacement operation, the orthopedic surgeon will dislocate the hip and expose both the head of the femur and the acetabulum. The acetabulum is reamed and surfaced with a hemispherical socket bonded to the adjacent pelvic bone structure by a cement such a polymethylmethacrylate (PMMA), commonly known as acrylic cement.

The head of the femur is removed from the femoral neck and the proximal end of the femur prepared to receive the femoral implant. This preparation includes forming an opening into the medullary canal of the femur to receive the implant.

The hip replacement techniques used today require the surgeon to size the canal formed in the femur such that a cement collar of at least 3-5 millimeters may be permitted to form and bond the implant to the femur. Once the surgeon is satisfied with the femoral canal that has provided for the chosen implant, and the positioning of that implant relative to the axis of to the femur and to the acetabular socket, current techniques require the physician to then remove the carefully positioned implant and to prepare a mixture of a bonding cement such as acrylic cement. The femoral canal is then recleaned, a bolus of the cement packed into the canal and the implant then repositioned in the femoral canal as the cement is hardening, hopefully again in the orientation which the surgeon previously determined to be correct. It is not unusual, however, for the implant to be finally seated in, and bonded to, the femur in a some-what different orientation than the surgeon previously determined to be correct. This in turn may well contribute to unusual forces being placed on the implant and on the acetabular socket to result in hip dislocation and failure of the implant, both of which are significant problems associated with hip replacement.

In marked contrast to these prior approaches to locating and bonding the implant within the femur, the present invention provides an implant which includes an interior channel 32 that is preferably cylindrical in shape, with its major axis parallel to the major axis of the stem portion and femur. The interior channel includes, at its proximal end, a threaded portion 34 the purpose of which will be described shortly. The internal channel extends well into the implant. About the internal channel preferably is provided a reduced area 36 in the surface of the implant, and at the distal end portion of this reduced area are opposed ports 38 which communicate with channel 32.

Figure 6:
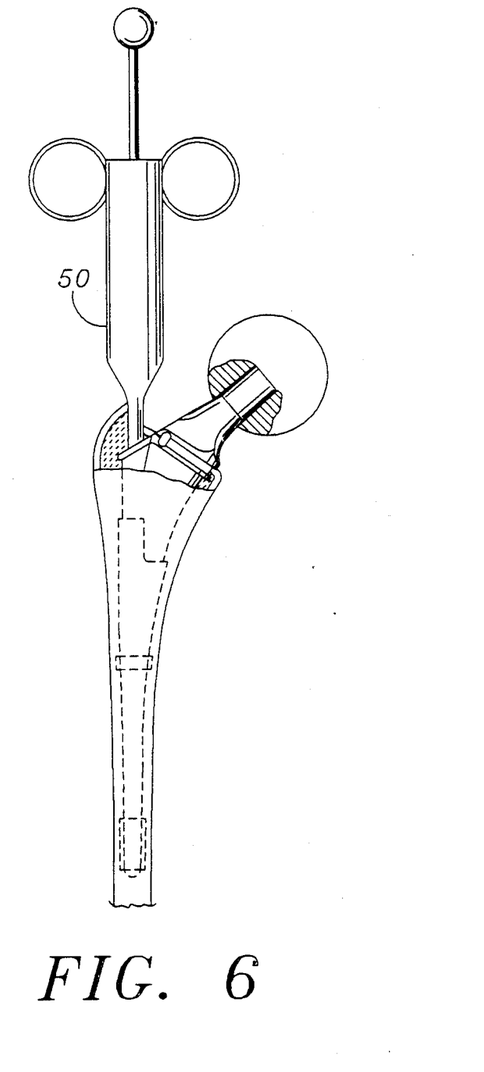
FIG. 6 is a view inpartial cross-section showing the femoral implant after it has been positioned in a prepared channel in the femur and is receiving cement discharged by an attached syringe into the implant.

After the surgeon has prepared a canal in the femur to receive the implant, and cleansed it of all bone chips, fragments and debris, the surgeon then inserts a cylindrical distal spacer 42 in the canal, positions a mid-stem spacer 44 about the insert, then slips the femoral insert 14 into the canal. If the surgeon has correctly chosen the sizes of the distal spacer and mid-stem spacer, the implant will be firmly received and seated in the femoral canal, the distal spacer wedging the distal end of stem 24 in the femoral canal and the mid-stem spacer wedging the medial or mid-portion of the implant in the femur; the mid-stem spacer also serves as a stop to prevent passage of cement down the femoral canal beyond that point. If the sizes of the chosen spacers do not achieve this result, the surgeon may easily remove the stem spacers, and select different size spacers and retry the fit until a proper fit is achieved. The surgeon checks to make sure that the longitudinal position of the implant relative to the femur is correct, and that its rotational position is also correct to properly position the head of the implant in the acetabular socket. This may require some readjustment of the femoral canal, or selection of a different size of implant. 11 of these steps proceed without the surgeon being under any time pressure; in the present technique, the surgeon is permitted to adjust and accurately position the implant relative to the femur without having to work against the time pressures imposed by a hardening cement collar about the implant.

Once the surgeon is satisfied with the implant and its location and fit in the femur, a batch of cement is prepared—typically acrylic cement is employed—and loaded in a syringe 50 such as shown in FIG. 6. The tip of this syringe is sized and threaded to be received in channel 32, and is screwed into threaded portion 34 to interlock syringe 50 with the implant. Preferably these steps follow immediately upon preparation of the cement; the cement is not allowed to begin to harden but instead is in its most fluid state. Pressure is then applied to the syringe plunger to force cement through the interior channel 32 of the implant and out its mid-portion ports. The cement flows about the implant, filling the cavity provided between the implant and the interior of the femur. Because the cement is relatively liquid and is being applied under pressure, it tends to readily enter the cancellous structure within the femur. It also floods retrograde up the cavity in the femur carrying upward on top of the cement bolus any debris remaining within the channel. In addition, a portion of the cement will tend to flow downwardly and about the implant, this portion filling all of the space below ports 38 and above the mid-stem spacer 44. Any cement which reaches the mid-stem spacer is prevented from further passage down the femoral canal by the mid-stem spacer.

Reduced area 36 in the implant provides an enlarged space or area for receiving the up-welling cement, and results in an enlarged predetermined collar of cement interlocking with the implant and bonding the implant to the femur. Preferably the proximal end portion of the implant is shaped, as by providing projecting wall portions 54 and 56, to apply some back-pressure to the cement bolus and to allow a consistent cement thickness to assist in achieving a secure bond of the implant within the femur.

As previously noted, preferably the implant includes an interior channel that, at its distal end, communicates with two ports 38, one being anteriorly located and the other one posteriorly located at the mid-portion of the implant. If desired, a third port 62 may also be provided in channel 32, being distally located relative to the femur canal and opening into the outer portion of the femoral cavity at the mid-portion of the implant. Thus, the implant of the present invention results in an accurately sized and positioned implant bonded to the proximal end of the femur. This proximal bonding results in normal stresses being applied to the proximal end of the femur and assists in maintaining the integrity of the femur throughout its remaining length.

When the implant has been bonded to the femur and cement cleaned from about the portion of the femoral canal adjacent the proximal end portion of the implant, the appropriate head 16 is seated on Morse taper 22 and the hip replacement operation concluded in the normal fashion.

The process for bonding a hip implant device within the femur during a hip replacement operation, as contemplated and taught by the present invention, provides an interior channel in the implant which communicates with ports for discharging bonding material into only the proximal portion of the femoral canal, to permit the implant to first be accurately located in the femur then bonding material to be discharged through the channel and ports to flood the proximal portion of the femoral canal while the implant remains in the previously established, proper position within the femur. Preferably the process includes employing spacers to assist in seating the implant within the femoral canal and to prevent passage of the bonding material distally down the femoral canal and beyond the stem.

Since variations in the preferred embodiment of the present invention will be apparent to those skilled in this art, the scope of the present invention should not be limited to the preferred embodiment just described, but rather is defined by the following claims.

We claim:

1. A femoral hip prosthetic implant for receipt in a femoral canal formed in a proximal end of a femur, the implant having a proximal end terminating in a neck portion for receiving a head, a mid-portion, and a distal end terminating in a stem portion, the implant including:
    at least one interior channel terminating in at least one port communicating with the exterior surface of the implant at said mid-portion and adjacent to the canal provided in the femur for receiving the implant,
    means for receiving and directing cement under pressure into the interior channel from the proximal end of the implant when the implant is received in a femur, and
    sealing means positioned around the mid-portion of said implant and located distally of each port of said interior channel and wedged between said mid-portion and the femur, said sealing means sized so as to block the passage of cement distally of said sealing means and down said femoral canal, such that said canal is devoid of cement distally of said sealing means,
    whereby the implant may be accurately positioned in the femoral canal, then cement forced through the interior channel to flood the canal proximally of said sealing means and well up under pressure to cleanse the canal of debris and to secure the implant to the femur at its proximal end.

2. A femoral hip prosthetic implant as set forth in claim 1 in which the main portion of the channel is generally straight and parallel to the axis of the stem portion of the implant.

3. A femoral hip prosthetic implant as set forth in claim 1 in which the means for receiving and directing the cement includes means for receiving and interlocking the implant with the end portion of a cement dispenser.

4. A femoral hip prosthetic implant as set forth in claim 3 in which the means for receiving and interlocking the implant with a cement dispenser comprises the end portion of the channel opening at the proximal end of the implant including internal threads to receive the threaded end portion of a cement dispenser.

5. A femoral hip prosthetic implant as set forth in claim 1, the implant including at least one reduced portion about the proximal end of said implant located proximally of said sealing means to receive and interlock with cement discharged through said port.

6. A femoral hip prosthetic implant as set forth in claim 5 in which said port opens into said reduced portion.

7. A femoral hip prosthetic implant as set forth in claim 6, the implant including multiple ports opening into said reduced portion on at least the anterior and posterior portions of the implant.

8. A femoral hip prosthetic implant as set forth in claim 1 in which said sealing means comprises a mid-stem spacer for being wedged between said mid-portion of the implant and the femoral canal, the spacer being shaped to hold the implant centered in the femoral canal.

9. A femoral hip prosthetic implant as set forth in claim 1 including spacer means about the stem portion to hold the implant in a fixed, centered position within the femoral canal.

10. A process for bonding a hip implant within a femoral canal formed in the proximal end of a femur, the implant including an interior channel to be interconnected at one end thereof with a source of cement under pressure and terminating at the opposite end with at least one port communicating with the exterior of said implant adjacent the femoral canal, said process including the steps of:
    locating sealing means about the approximate mid-portion of said implant distally of each port of said interior channel;
    positioning the implant within the femoral canal, such that said sealing means is wedged between said implant and said femur and sized to block the passage of cement distally therepast and down said canal, whereby said canal will be devoid of cement distally of said sealing means; and forcing cement under pressure from a source thereof through the interior channel and outwardly of said at least one port thereof to fill only that portion of the femoral canal between the implant and the femur which is located proximally of said sealing means.

11. A process for bonding a hip implant within a femoral canal as set forth in claim 10, including the additional step of providing said implant with a reduced surface portion thereabout and located proximally of said sealing means to receive and interlock with the cement discharged through said port, said reduced portion resulting in an enlarged consistent collar of cement within the femoral canal at the proximal end of the femur.

12. A process for bonding a hip implant within a femoral canal as set forth in claim 10, including the additional step of locating spacer means about said implant distally of said sealing means to engage the femur and hold the implant in a fixed, centered position within the femoral canal.

* * * * *

UNITED STATES PATENT AND TRADEMARK OFFICE
CERTIFICATE OF CORRECTION

PATENT NO.  : B1-5,133,772
DATED       : August 5, 1997
INVENTOR(S) : Hack, et al It is certified that error appears in the above-identified patent and that said Letters Patent is hereby corrected as shown below:

On the title page, items [58] Field of Search, line 2, "62323" should read -- 623/23 --.

item [57] Abstract, line 12, "portions" should read -- portion --.

Signed and Sealed this

Third Day of March, 1998

Attest:

BRUCE LEHMAN

*Attesting Officer*    Commissioner of Patents and Trademarks

REEXAMINATION CERTIFICATE (3289th)

United States Patent [19]
Hack et al.

[11] B1 5,133,772
[45] Certificate Issued Aug. 5, 1997

[54] FEMORAL IMPLANT FOR HIP ARTHROPLASTY

[75] Inventors: Bradford H. Hack, Arcadia; Philip O. Merritt, Los Angeles, both of Calif.

[73] Assignee: Osteonics Corporation, Allendale, N.J.

Reexamination Request:
No. 90/004,118, Jan. 24, 1996

Reexamination Certificate for:
Patent No.: 5,133,772
Issued: Jul. 28, 1992
Appl. No.: 466,036
Filed: Jan. 17, 1990

[51] Int. Cl.$^6$ ............................................. A61F 2/32
[52] U.S. Cl. ............................................. 623/23
[58] Field of Search ................... 623/16, 18, 20, 623/23; 606/92, 93, 94, 95

[56] References Cited

U.S. PATENT DOCUMENTS

| | | |
|---|---|---|
| 4,245,359 | 1/1981 | Stuhmer . |
| 4,274,163 | 6/1981 | Malcom et al. . |
| 4,494,535 | 1/1985 | Haig . |
| 4,523,587 | 6/1985 | Frey . |
| 4,650,489 | 3/1987 | Thompson . |
| 4,653,487 | 3/1987 | Maale . |
| 4,718,909 | 1/1988 | Brown . |
| 4,753,657 | 6/1988 | Lee et al. . |
| 4,783,192 | 11/1988 | Wroblewski et al. . |
| 4,881,536 | 11/1989 | Noble et al. . |
| 4,888,022 | 12/1989 | Huebsch . |
| 4,983,183 | 1/1991 | Horowitz . |
| 4,988,359 | 1/1991 | Frey et al. . |
| 4,994,085 | 2/1991 | Sawai et al. . |
| 4,997,448 | 3/1991 | Feiler . |
| 5,047,061 | 9/1991 | Brown . |
| 5,061,287 | 10/1991 | Feiler . |
| 5,108,437 | 4/1992 | Kenna . |
| 5,314,494 | 5/1994 | Huiskes et al. . |

FOREIGN PATENT DOCUMENTS

| | | |
|---|---|---|
| 0357546A1 | of 1989 | European Pat. Off. . |
| 0434604A1 | of 1990 | European Pat. Off. . |
| 2614524A1 | of 1988 | France . |
| 1424829A1 | of 1988 | U.S.S.R. . |

OTHER PUBLICATIONS

"Femoral Strain Patterns with Press–Fit THR — A Photoelastic Analysis," Zhou, X–M, Robertson, D.D., Walker, P.S., 34th Annual Meeting Orthopaedic Research Society, Feb. 1–4, 1988, Atlanta, Georgia.

"Design And Fabrication Of Cementless Hip Stems," Walker, P.S. and Robertson, D.D., Clinical Orthopaedics and Related Search, No. 235, Oct., 1988.

"The Effect Of A Thin Coating Of Polymethylmethacrylate On The Torsional Fatigue Strength Of The Cement–Metal Interface," Davies, Singer and Harris, Journal of Applied Biomaterials, received Feb. 14, 1991, accepted Oct. 22, 1991.

"Peak Cement Strains In Cemented Femoral Total Hip," O'Connor, Burke et al., 37th Annual Meeting, Orthopaedic Research Society, Mar. 4–7, 1991, Anaheim, California.

"The Scientific Basis of Cement Versus Cementless Fixation," Freeman and Tennant, Clinical Orthopaedics and Related Research, No. 276, Mar., 1992 (received Dec. 7, 1990).

"The Influence of Stem Size and Extent of Porous Coating on Femoral Bone Resorption after Primary Cementless Hip Arthroplasty," Engh and Bobyn, Clinical Orthopaedics and Related Research, No. 231, Jun., 1988.

*Primary Examiner*—David J. Isabella

[57] ABSTRACT

The present invention concerns a femoral hip prosthetic implant, and a process, that incorporates an interior channel in the implant, which channel permits the implant, after it is properly positioned in a canal at the proximal end of a prepared femur, to be left in that position. Cement is then injected through that channel and discharged through medial ports in the implant to flood and up-well in the space between the implant and the femoral canal, thereby bonding and sealing the implant to the proximal portion of the femur while the implant remains seated in the desired position within the femur. Preferably a collar is provided at the distal portions of the stem to firmly seat and center the stem within the femoral canal. Also, preferably a spacer is provided at the mid-portion of the stem to center the stem within the femoral canal and to prevent cement from passing down the femoral canal beyond the proximal end of the stem.

B1 5,133,772

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1-7, 10, 11 is confirmed.

Claims 8, 9, and 12 are determined to be patentable as amended.

New claims 13-18 are added and determined to be patentable.

8. A femoral hip prosthetic implant as set forth in claim 1 in which said sealing means comprises a mid-stem spacer for being wedged between said mid-portion of the implant and the femoral canal, the spacer being shaped to hold the implant centered in the femoral canal *at least in the area of the mid-portion*.

9. A femoral hip prosthetic implant as set forth in claim 1 including spacer means about the stem portion to hold the implant in a fixed, centered position within the femoral canal *at least in the area of the spacer means*.

12. A process for bonding a hip implant within a femoral canal as set forth in claim 10, including the additional step of locating spacer means about said implant distally of said sealing means to engage the femur and hold the implant in a fixed, centered position with the femoral canal *at least in the area of the spacer means*.

*13. A process for bonding a hip implant within a femoral canal as set forth in claim 12 including the additional step of providing sealing means which comprise a mid-stem spacer, and wedging the mid-stem spacer between the mid-portion of the implant and the femoral canal, whereby the mid-stem spacer and the spacer means together hold the implant centered in the femoral canal.*

*14. The femoral hip prosthetic implant as set forth in claim 9 in which said spacer means is located about the stem portion of said implant distally of said sealing means.*

*15. The femoral hip prosthetic implant as set forth in claim 14 in which said sealing means comprises a mid-stem spacer for being wedged between said mid-portion of the implant and the femoral canal, whereby said spacer means and said mid-stem spacer together center the implant in the femoral canal.*

*16. A femoral hip prosthetic implant for receipt in a femoral canal formed in a proximal end of a femur, the implant having a proximal end terminating in a neck portion for receiving a head, a mid-portion, and a distal end terminating in a stem portion, the implant including:*

*at least one interior channel terminating in at least one port communicating with the exterior surface of the implant at said mid-portion and adjacent to the canal provided in the femur for receiving the implant,*

*means for receiving and directing cement under pressure into the interior channel from the proximal end of the implant when the implant is received in a femur,*

*sealing means positioned around the mid-portion of said implant and located distally of each port of said interior channel and wedged between said mid-portion and the femur, said sealing means sized so as to block the passage of cement distally of said sealing means and down said femoral canal, such that said canal is devoid of cement distally of said sealing means,*

*at least one reduced portion about the proximal end of said implant located proximally of said sealing means to receive an interlock with cement discharged through said port, and*

*whereby the implant may be accurately positioned in the femoral canal, then cement forced through the interior channel to flood the canal proximally of said sealing means and well up under pressure to cleanse the canal of debris and to secure the implant to the femur at its proximal end.*

*17. A femoral hip prosthetic implant as set forth in claim 16 in which said port opens into said reduced portion.*

*18. A femoral hip prosthetic implant as set forth in claim 17, the implant including multiple ports opening into said reduced portion on at least the anterior and posterior portions of the implant.*

* * * * *